US011116844B2

(12) United States Patent
Boday et al.

(10) Patent No.: US 11,116,844 B2
(45) Date of Patent: Sep. 14, 2021

(54) MACROMOLECULAR CHEMOTHERAPEUTICS

(71) Applicants: International Business Machines Corporation, Armonk, NY (US); Agency for Science, Technology and Research, Singapore (SG)

(72) Inventors: Dylan Boday, Tucson, AZ (US); Wei Cheng, Singapore (SG); Jeannette M. Garcia, San Leandro, CA (US); James Hedrick, Pleasanton, CA (US); Nathaniel H. Park, San Jose, CA (US); Rudy J. Wojtecki, San Jose, CA (US); Chuan Yang, Hillington Green (SG); YiYan Yang, Singapore (SG)

(73) Assignees: INTERNATIONAL BUSINESS MACHINES CORPORATION, Armonk, NY (US); AGENCY FOR SCIENCE, TECHNOLOGY, Singapore (SG)

( * ) Notice: Subject to any disclaimer, the term of this patent is extended or adjusted under 35 U.S.C. 154(b) by 0 days.

(21) Appl. No.: 16/577,142

(22) Filed: Sep. 20, 2019

(65) Prior Publication Data
US 2020/0023069 A1 Jan. 23, 2020

Related U.S. Application Data

(62) Division of application No. 15/807,602, filed on Nov. 9, 2017, now Pat. No. 10,463,746.

(51) Int. Cl.
| | | |
|---|---|---|
| *A61K 47/60* | (2017.01) |
| *A61K 47/69* | (2017.01) |
| *A61K 31/785* | (2006.01) |
| *A61P 35/00* | (2006.01) |
| *C08G 65/332* | (2006.01) |
| *C08G 65/00* | (2006.01) |
| *C08L 71/02* | (2006.01) |
| *C08G 64/18* | (2006.01) |
| *C08L 71/00* | (2006.01) |
| *A61K 9/107* | (2006.01) |

(52) U.S. Cl.
CPC ............ *A61K 47/60* (2017.08); *A61K 9/1075* (2013.01); *A61K 31/785* (2013.01); *A61K 47/6907* (2017.08); *A61P 35/00* (2018.01); *C08G 64/183* (2013.01); *C08G 65/00* (2013.01); *C08G 65/332* (2013.01); *C08G 65/3328* (2013.01); *C08L 71/00* (2013.01); *C08L 71/02* (2013.01); *C08G 2650/44* (2013.01)

(58) Field of Classification Search
None
See application file for complete search history.

(56) References Cited

U.S. PATENT DOCUMENTS

| | | |
|---|---|---|
| 8,044,194 B2 | 10/2011 | Dubois et al. |
| 8,088,412 B2 | 1/2012 | Forrest et al. |
| 8,207,351 B2 | 6/2012 | Fujiwara et al. |
| 8,226,985 B2 | 7/2012 | Fukushima et al. |
| 8,415,400 B2 | 4/2013 | Bronich et al. |
| 8,455,612 B2 | 6/2013 | Fujiwara et al. |
| 8,470,891 B2 | 6/2013 | Hedrick et al. |
| 8,476,428 B2 | 7/2013 | Hedrick et al. |
| 8,633,296 B1 | 1/2014 | Coady et al. |
| 8,940,855 B2 | 1/2015 | Hedrick et al. |
| 8,962,772 B2 | 2/2015 | Ding et al. |
| 9,272,043 B2 | 3/2016 | Saltzman et al. |
| 9,278,067 B2 | 3/2016 | Boulikas |
| 9,334,367 B2 | 5/2016 | Davis et al. |
| 10,463,746 B2 * | 11/2019 | Boday ............... A61K 47/6907 |
| 2004/0185564 A1 | 9/2004 | Tang et al. |
| 2009/0232762 A1 | 9/2009 | Xiong et al. |
| 2009/0258416 A1 | 10/2009 | Kataoka et al. |
| 2014/0350077 A1 * | 11/2014 | Cooley ............... A61K 47/593 514/44 A |
| 2015/0098976 A1 | 4/2015 | Ding et al. |
| 2015/0110713 A1 | 4/2015 | Manganaro et al. |
| 2015/0209440 A1 | 7/2015 | Eliasof et al. |
| 2016/0220705 A1 | 8/2016 | Chan et al. |
| 2016/0338356 A1 | 11/2016 | Xin Ding et al. |
| 2019/0134210 A1 | 5/2019 | Boday et al. |

FOREIGN PATENT DOCUMENTS

| | | |
|---|---|---|
| CN | 104780926 A | 7/2015 |
| CN | 104906075 A | 9/2015 |
| CN | 105101976 A | 11/2015 |
| CN | 105101988 A | 11/2015 |
| WO | 2005084710 A2 | 9/2005 |

(Continued)

OTHER PUBLICATIONS

Voo et al., Macromolecules, 2015, 48(4), pp. 1055-1064. (Year: 2015).*
Frère et al., Biomacromolecules, 2015, vol. 16, pp. 769-779. (Year: 2015).*
Frère et al., Biomacromolecules, 2015, vol. 16, Abstract only. (Year: 2015).*
Engler, Amanda C. et al., Hydrophilic Polycarbonates: "Promising Degradable Alternatives to Poly(ethylene glycol)—Based Stealth Materials", Macromolecules 2015, 48, 1673-1678.

(Continued)

*Primary Examiner* — Brian Gulledge
(74) *Attorney, Agent, or Firm* — Cantor Colburn LLP; Kristofer Haggerty

(57) ABSTRACT

Embodiments of the invention are directed to a macromolecular chemotherapeutic. A non-limiting example of the macromolecular chemotherapeutic includes a block copolymer. The block copolymer can include a water-soluble block, a cationic block, and a linker, wherein the linker is connected to the water-soluble bock and the charged block.

19 Claims, 9 Drawing Sheets

(56) References Cited

FOREIGN PATENT DOCUMENTS

| WO | 2015042252 A1 | 3/2015 |
| WO | 2016118697 A1 | 7/2016 |
| WO | 2016186581 A1 | 11/2016 |

OTHER PUBLICATIONS

International Search Report and Written Opinion for International Application No. PCT/IB2018/058479; International filing date: Oct. 30, 2018; dated Feb. 12, 2019; 14 pgs.

Li, Yan et al., "Broad-Spectrum Antimicrobial and Biofilm-Disrupting Hydrogels; Stereocomplex-Driven Supramolecular Assemblies", Angew. Chem. Int. Ed. 2013, 52, 674-678.

List of IBM Patents or Patent Applications Treated as Related; (Appendix P), Date Filed Sep. 23, 2019; 2 pages.

Voo, et al. "Antimicrobial/Antifouling Polycarbonate Coatings: Role of Block Copolymer Architecture" ACS Publications, Macromolecules 2015, 28, 1055-1064, pp. 1-10.

\* cited by examiner

MACROMOLECULAR CHEMOTHERAPEUTICS

DOMESTIC PRIORITY

This application is a Divisional of U.S. patent application Ser. No. 15/807,602 filed Nov. 9, 2017, the disclosure of which is incorporated by reference herein in its entirety.

BACKGROUND

The present invention relates in general to chemotherapeutics, and more specifically, to macromolecular chemotherapeutics.

With increased incidence of cancer, the development of new approaches to cancer therapy has garnered increasing importance for advancing quality patient care. Although several chemotherapeutics have demonstrated efficacy in treating cancer, several issues have presented challenges to the development of safe and effective chemotherapeutics. Such issues include, for example, aggressive resistance development to drugs or drug cocktails, significant off-target toxicity of chemotherapeutics, and solubility and delivery issues, including insufficient drug accumulation in tumor tissue and rapid clearance from the body.

The design of a simple yet highly efficacious system for cancer therapy remains a challenging endeavor. Moreover, a need remains for chemotherapeutic systems that maintain efficacy after repeated exposure. A need also exists for chemotherapeutic agents with efficacy against cancer stem cells.

SUMMARY

Embodiments of the invention are directed to a macromolecular chemotherapeutic. A non-limiting example of the macromolecular chemotherapeutic includes a block copolymer. The block copolymer can include a water-soluble block, a cationic block, and a linker, wherein the linker is connected to the water-soluble bock and the charged block.

Embodiments of the invention are directed to a pharmaceutical composition. A non-limiting example of the pharmaceutical composition includes a block copolymer. The block copolymer can include a water-soluble block, a cationic block, and a linker, wherein the linker is connected to the water-soluble bock and the charged block.

Embodiments of the invention are directed to a method of treating cancer. Non-limiting examples of the method include administering to a mammal in need thereof an effective amount of a pharmaceutical composition. A non-limiting example of the pharmaceutical composition includes a block copolymer. The block copolymer can include a water-soluble block, a cationic block, and a linker, wherein the linker is connected to the water-soluble bock and the charged block.

Embodiments of the invention are directed to a method of synthesizing a chemotherapeutic agent. Non-limiting examples of the method include forming a mixture comprising a cyclic carbonyl monomer comprising a cyclic carbonyl group having a cationic sidechain with a macroinitiator selected from the group consisting of a polyethylene glycol comprising an acetal and a methoxypoly(ethylene glycol), and an organocatalyst. Non-limiting examples of the method also include agitating the mixture at a time sufficient to form a block copolymer.

Embodiments of the invention are directed a block copolymer. Non-limiting examples of the block copolymer include molecules of formula (I):

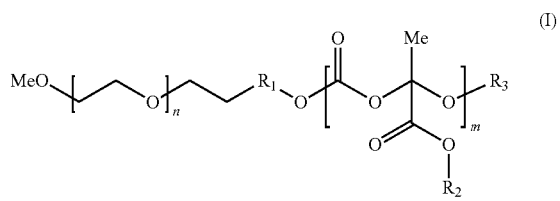

wherein n is an integer ranging from 45 to 460, R1 is selected from the group consisting of an acetal and an ether, R2 is a positively charged alkane bearing one or more nitrogen or sulfur atoms, m is an integer ranging from 5 to 200, and R3 is hydrogen, a polylactide, or a cholesterol.

Embodiments of the invention are directed to a method of inhibiting cancer stem cell growth. The exemplary method includes providing a culture of cancer cells including a plurality of cancer stem cells. The method also includes incubating the cancer stem cells with a solution including a plurality of micelles, including block copolymers including a water soluble block, a cationic block, and a cleavable linker, wherein the cleavable linker is connected to the water-soluble block and the charged block.

BRIEF DESCRIPTION OF THE DRAWINGS

The foregoing and other features and advantages of the embodiments of the invention are apparent from the following detailed description taken in conjunction with the accompanying drawings in which.

DETAILED DESCRIPTION

Figure 1B:
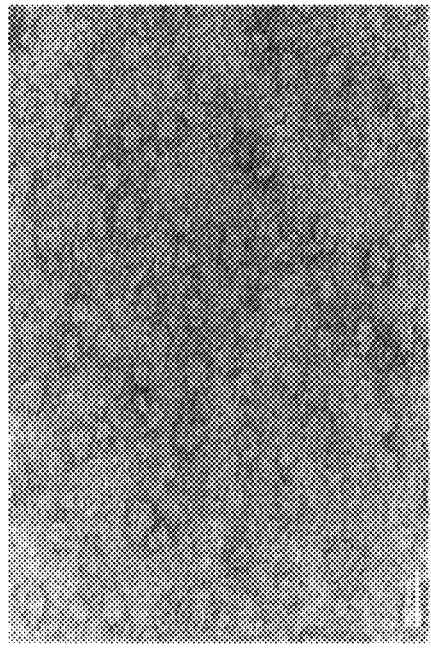
FIG. 1B depicts TEM image of macromolecular chemotherapeutics according to exemplary embodiments of the invention.

A number of drug delivery systems that involve nanotechnology have been investigated in attempts to increase drug solubility, increase circulation half-life, increase accumulation in tumor tissue, and reduce drug toxicity. Such systems have a number of shortcomings, many of which derive from the systems' continued reliance on the action of chemotherapeutic drugs that have inherent limitations that cannot be overcome through the addition of nanotechnology components. For example, while a nanotechnology delivery system has potential to increase the concentration of a chemotherapeutic in tumor tissue, effectiveness of such a system can yet be limited by cellular barriers and resistance mechanisms. Moreover, drug delivery systems, including those that employ nanotechnology, can be prone to other drawbacks such as burst release, potential off-target toxicity, and low circulation half-lives.

Despite the demonstrated efficacy of chemotherapy in treating cancer, it can be plagued by numerous issues that hinder the development of effective, personalized therapeutic regimes. These issues include aggressive resistance development to drugs or drug cocktails, insufficient drug accumulation in tumor tissue, low aqueous solubility of some chemotherapeutics, rapid clearance from the body, and significant off-target toxicity. The push to overcome these issues has led to the development of an extensive array of nanotechnology drug delivery systems that aim to increase drug solubility, circulation half-life, accumulation in tumor tissue, as well as reduce the toxicity of the drug itself. The success of nanotechnology therapeutics has resulted in several systems reaching clinical trials or garnering FDA approval for human use.

While efficacious nanotechnology systems have been demonstrated, many such approaches rely on complex strategies involving multi-functional nanoparticles, the loading of several small molecule chemotherapeutics or chemo sensitizing agents, or require significant synthetic efforts to access the necessary materials. Moreover, nanotechnology systems must also meet stringent biocompatibility requirements before administration to a human.

Recent studies have identified potential differences between the activity of chemotherapeutic agents on cancer stem cells and non-stem cells. For example, studies have suggested that a continued problem with many chemotherapeutic agents is that despite their ability to kill general cancer cells, they can sometimes enhance the growth of cancer stem cells.

Turning now to an overview of the aspects of the invention, one or more embodiments of the invention address the above-described shortcomings of the prior art by providing a biocompatible system including a cationic polymer that can have potent anticancer activity.

In some embodiments of the invention, macromolecular chemotherapeutics are provided that include a water soluble block, such as a hydrophilic polyethylene glycol (PEG) block, a linker, and a cationic block. In some embodiments of the invention, the cationic block is built from a polycarbonate scaffold. The macromolecular chemotherapeutics, for example, can form micelles.

Upon administration, the macromolecular chemotherapeutics according to embodiments of the invention can circulate through the bloodstream and selectively accumulate in tumor tissue via the EPR effect. In the vascularized tissue, the macromolecular chemotherapeutics can undergo endocytosis by the cancer cells. In some embodiments of the invention, macromolecular chemotherapeutics include a linker that is a pH sensitive linker. A pH sensitive linker can trigger cleavage of the water soluble block from the cationic block in the cancer cells, for example when the environmental pH is lowered upon entry into the cells. The released cationic polymer can associate with the interior leaflet of the cancer cell membrane, causing disruption and eventual lysis of the cell itself. Embodiments of the invention can kill cancer cells by necrosis. Killing cancer cells by necrosis, for instance instead of via apoptosis, can advantageously reduce the development of resistance to the anticancer agent.

In some embodiments of the invention, macromolecular chemotherapeutics can have potent antitumor activity. For example, the PEG block can protect the cationic core and enhance circulation times, enabling passive tumor accumulation. Additionally, positively charged, drug-loaded micelles or micelles formulated with cationic lipids have shown increased uptake by tumor tissue. Desirably, macromolecular chemotherapeutics can have anticancer activity without the need to complex the macromolecular structures with potentially toxic and non-soluble small molecule anticancer agents. Moreover, macromolecular chemotherapeutics can show potent activity against cancer stem cells.

Macromolecular chemotherapeutics according to embodiments of the invention include block copolymers. The block copolymers can include a water-soluble block, a charged block, and a cleavable linker. In some embodiments of the invention, block copolymers are represented by the structure:

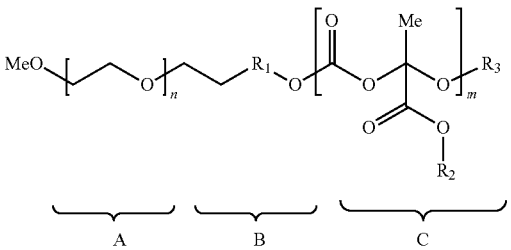

wherein A represents a water-soluble block, B represents a cleavable linker, and C represents a cationic block, and wherein n is an integer ranging from 5 to 560, m is an integer ranging from 5 to 200, R1 is a cleavable or non-cleavable linker, such as an acetal or an ether, R2 is a cationic group, such as a positively charged alkane bearing one or more nitrogen or sulfur atoms, and R3 is hydrogen, a neutral polycarbonate block, or a polylactide block, or an endcap.

Embodiments of the invention include a block copolymer including a water-soluble block. In some embodiments, the water soluble block includes a polyethylene oxide. In some embodiments of the invention, the water soluble block includes a plurality of poly(ethylene glycol) (PEG) subunits or methoxypolyethylene glycol (mPEG) subunits. In some embodiments of the invention, water soluble block includes a plurality of subunits according to formula (A-1):

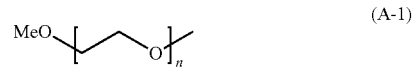

wherein n is an integer ranging from 5 to 1000, or from 50 to 500, or from 100 to 200. In some embodiments, for example, the water soluble block has an average molecular weight from 500 to 50,000 Daltons (Da), such as 2,000 to 10,000 Da, or 5000 Da.

In some embodiments, water soluble block includes water soluble carbonates, such as carbonates of formula (A-2):

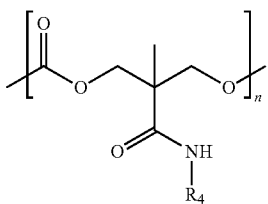
(A-2)

wherein n is an integer ranging from 5 to 500 and R4 is a hydroxyl group or C1 to C4 alcohol or glycol, such as ethanol, propanol, butanol, isopropanol, isobutanol, or propylene glycol.

Embodiments of the invention include a block copolymer including a cleavable linker connected to the water-soluble block and the cationic block. The linker can be any acid cleavable group or redox cleavable group. In some embodiments of the invention, macromolecular chemotherapeutic includes a linker according to formula (B-1):

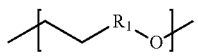
(B-1)

wherein R1 can be, for instance, carbon, an alkane, such as a C2 to C4 linear or branched alkane, an acetal or an ether. Exemplary linkers include, for instance, units of the following structures:

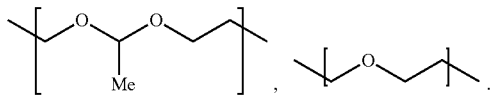

Embodiments of the invention include a block copolymer including a cationic block. The polymer backbone portion of the cationic block can include a carbonate group or a carbamate group, such as a carbonate derived from a 6 membered or 8 membered cyclic ring. Cationic block can include a charged block or a mixed charged block and can be homogeneous or heterogeneous.

The cationic block can be highly water-soluble or possess amphiphilic properties conducive to micelle formation in aqueous media. In some embodiments of the invention, the cationic block includes a hydrophobic component. In some embodiments, the hydrophobic component of the cationic block includes a C1 to C12 alkyl group. In some embodiments of the invention, the hydrophobic component of the cationic block includes a cholesterol, bile acid, functionalized sterol derivative, or lipid.

In some embodiments of the invention, cationic block includes cationic subunits of formula (C-1):

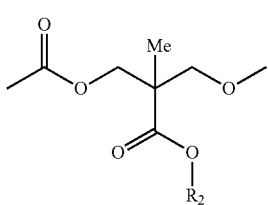
(C-1)

wherein R2 can include a positively charged alkane, such as a C4 to C50 alkane bearing, for example, nitrogen and/or sulfur. In some embodiments of the invention, for example, the cationic block includes a positively charged organic group including, for instance, a linear alkane, such as an octyl, hexyl, or butyl group; cholesterol; lithocholic group; palmitoyl group; oleyl group; alpha-tocopherol; guanidinium and/or isothiouronium group; and combinations and derivatives thereof, each bearing for instance one or more positively charged nitrogen atoms.

In some embodiments, R2 is a structure of the formula (C-2):

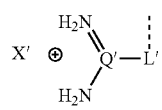
(C-2)

wherein L' is a divalent hydrocarbon radical having 2 to 30 carbons, Q' is *—N(H)—* or *—S—*, X' is a negatively charged counterion, and Y' is a single bond, *—O—* or *—N(H)—*.

Exemplary non-limiting L' groups include 1,2-ethylene, 1,2-propylene, 1,3-propylene, 1,2-butylene, 1,3-butylene, 1,4-butylene, 1,2-pentylene, 1,3-pentylene, 1,4-pentylene, 1,5-pentylene, 1,2-cyclohexylene, 1,3-cyclohexylene, 1,4-cyclohexylene, 1,2-phenylene, 1,3-phenylene, and 1,4-phenylene. In some embodiments of the invention, L' is an alkylene group of formula (C-3):

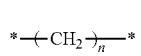
(C-3)

wherein n is an integer having a value from 2 to 6. In some embodiments of the invention, L' is 1,2-ethylene.

Non-limiting exemplary negatively charged counterions X' include halides (e.g., fluoride, chloride, bromide, iodide), hydroxide, alkyl or aryl carboxylates (e.g., trifluoroacetate, pentafluorobenzoate), hydrogen carbonate, alkyl and aryl sulfonates (e.g., methanesulfonate, p-toluenesulfonate), methyl sulfate, hydrogen sulfate, nitrate, dihydrogen phosphate, dialkyle and diaryl phosphates, and alkyl and aryl phosphonates.

As used herein, guanidinium group refers to a positively charged protonated guanidine group. As used herein, isothiouronium group refers to a positively charged protonated isothiourea group. For example, in some embodiments of the invention, the cationic block includes a pendant hydrosalt of a guanidine or isothiourea group. A hydrosalt of a guanidine or isothiourea group includes a positively charged protonated form of a guanidine or isothiourea that is ionically associated with a negatively charged counterion.

A hydro salt of a guanidine group can be depicted by the structure:

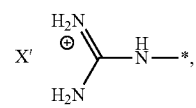

wherein X' is a negatively charged counterion. Herein, a bond with an asterix is referred to as a starred bond. Starred bonds are not methyl groups. An atomic center including a starred bond indicates the atomic center is covalently linked to another portion of the chemical structure. For example, in the above structure, the nitrogen adjacent the starred bond can be covalently linked to another portion of the side chain of the cationic block.

A hydro salt of an isothiourea group can be depicted by the structure:

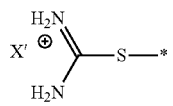

wherein X' is a negatively charged counterion and the sulfur adjacent the starred bond can be covalently linked to another portion of the side chain of the cationic block. As illustrated, each negatively charged counterion X' represents an independent ion and is also a "free ion," meaning X' is not covalently linked directly or indirectly to the backbone of the cationic polymer.

In some embodiments of the invention, cationic block is a charged block with the following formula (C-4):

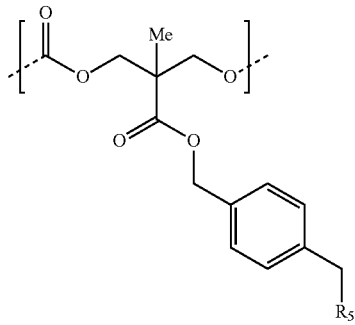

wherein and R5 is a positively charged nitrogen bearing alkane, such as a nitrogen bearing butyl, hexyl, or octyl, DABCO-propyl, DABCO-hexyl, palmitoyl, cholesterol, or lithocholic group.

For example, R5 can include compounds of the following structures:

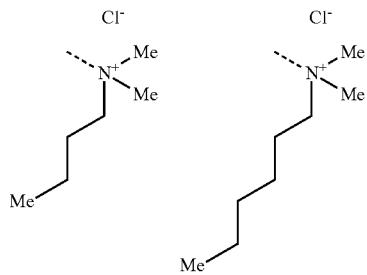

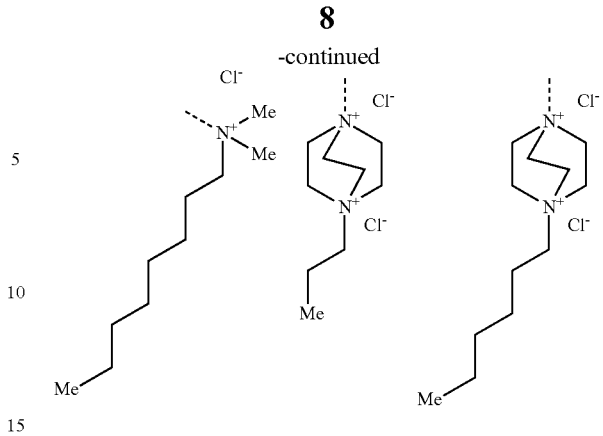

In some embodiments of the invention, a cationic block is bonded to a block capable of driving micellar assembly, such as a charged or uncharged block having one or more stereocenters. For instance, in some embodiments, macromolecular chemotherapeutics include block copolymer subunits including a cationic block as described herein bonded to a block of the following formulae (D-1) and (D-2), including D- and L-lactide blocks respectively:

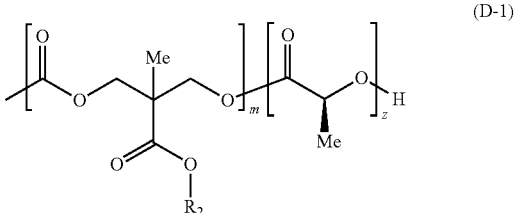

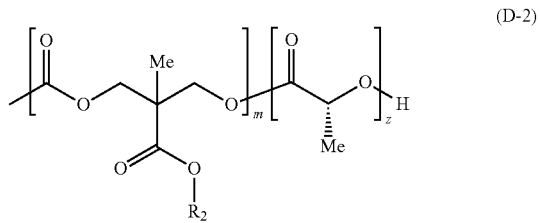

wherein m is an integer ranging from 10 to 100, z is an integer ranging from 10 to 100, and R2 is a group as described above.

In some embodiments of the invention, R2 is a group according to the following structure:

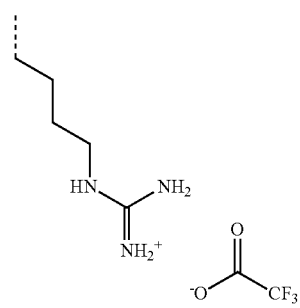

In some embodiments of the invention, cationic block is an ordered copolymer. In some embodiments, of the invention, cationic block is a random copolymer. The cationic block can include cationic subunits singularly or in combination. The cationic block can be a mixed charged block, such as an AB diblock copolymer unit or an ABC triblock copolymer unit.

In some embodiments of the invention, a cationic subunit is bonded to a neutral polycarbonate block. For example, an exemplary macromolecular chemotherapeutic includes a polymer of formula (E-1):

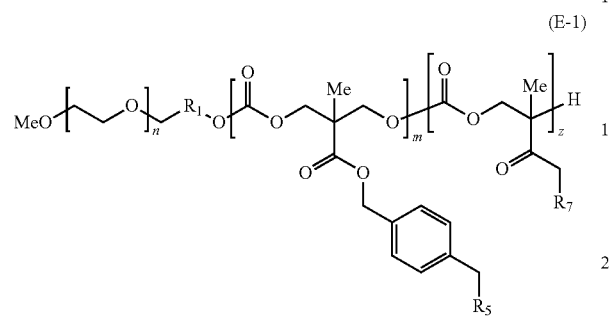

(E-1)

wherein m is an integer ranging from 2-15, R7 is an aliphatic group, such as a neutral long chain (C5 to C50) alkyl group, or a cholesterol, z is an integer ranging from 1 to 2, and n, R1, and R5 are as described herein above. In some embodiments of the invention, R7 is an octyl group or an oleyl group. In some embodiments of the invention, R7 includes alpha-tocopherol (Vitamin E).

In some embodiments of the invention, macromolecular chemotherapeutics include an end cap. The endcap can be bound to the cationic subunit or to a unit adjacent to the cationic subunit. For example, a macromolecular chemotherapeutic can include a polymer of formula (E-2):

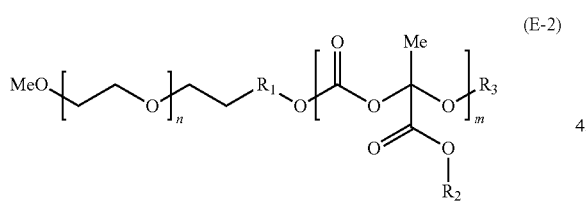

(E-2)

wherein the endcap is denoted as R3 and can include a compound of formula (E-3):

(E-3)

in which R8 can include a long chain alkyl group, a neutral polycarbonate, or cholesterol. In some embodiments of the invention, R8 is selected to drive micellar formation. For example, cholesterol or vitamin E can drive micellar formation in some embodiments of the invention.

Some embodiments of the invention include a polymer of formula (M-1):

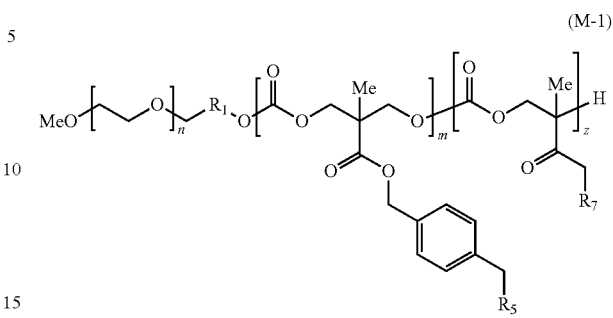

(M-1)

in which n is an integer ranging from 45 to 460, m is an integer ranging from 2 to 15, R5 contains a positively charged nitrogen atom bonded to an octyl or oleyl group containing cationic charge, and z is an integer ranging from 1 to 2.

Some embodiments of the invention include a polymer of formula (M-2):

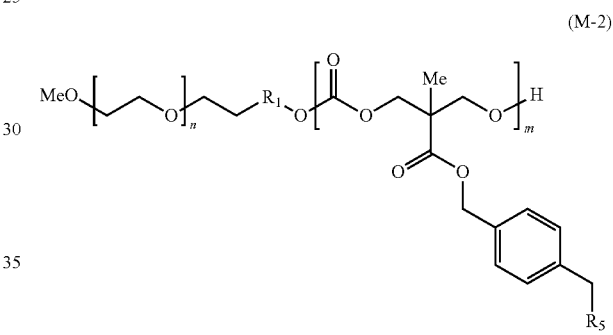

(M-2)

in which n is an integer selected such that the PEG subunit has an average molecular weight of about 5,000 Da, R1 is acetal or ether, and R5 contains a positively charged nitrogen atom bonded to a butyl, hexyl, octyl, DABCO-propyl, DABCO-hexyl, palmitoyl, cholesterol, or lithocholic group.

Some embodiments of the invention include a polymer of formula (M-3):

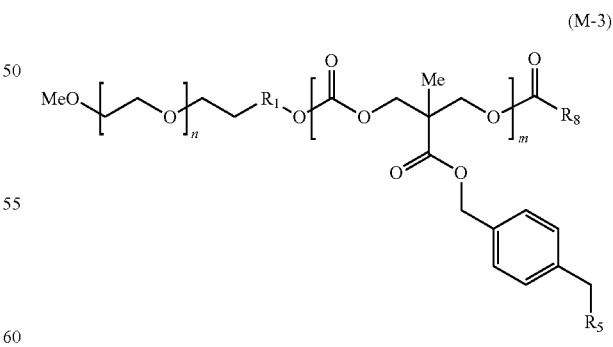

(M-3)

in which n is an integer selected such that the PEG subunit has an average molecular weight of about 5,000 Da, R1 is acetal or ether, m is 10, R5 contains a positively charged nitrogen atom bonded to a butyl, hexyl, octyl, DABCO-propyl, DABCO-hexyl, palmitoyl, cholesterol, or lithocholic group, and R8 is cholesterol.

In some embodiments of the invention, macromolecular chemotherapeutic includes a polymer of formula (M-4):

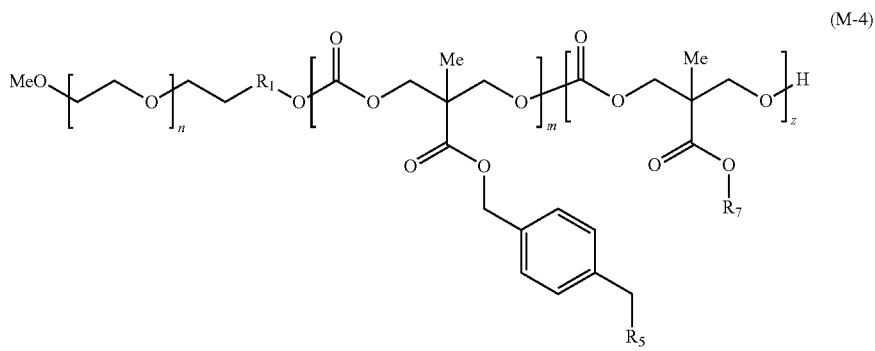

(M-4)

in which n is an integer selected such that the PEG subunit has an average molecular weight of about 5,000 Da, R1 is acetal or ether, m is an integer ranging from 2 to 15, R5 contains a positively charged nitrogen atom bonded to a butyl, hexyl, octyl, DABCO-propyl, DABCO-hexyl, palmitoyl, cholesterol, or lithocholic group, R7 is alpha-tocopherol, and z is an integer ranging from 1 to 2.

Macromolecular chemotherapeutic polymers can include non-stereospecific and/or stereospecific repeat units. A stereospecific repeat unit includes a non-superimposable mirror image and can include one or more asymmetric tetravalent carbons. The asymmetric tetravalent carbons can be assigned an R or S symmetry based upon Cahn-Ingold-Prelog symmetry rules. Some embodiments of the invention include a stereocomplex including polymers of formulae (M-5) and (M-6):

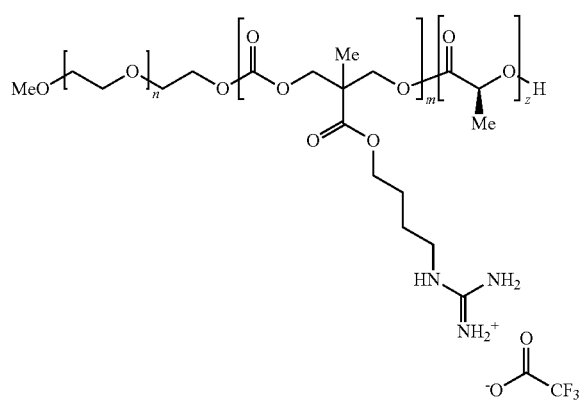

(M-5)

-continued

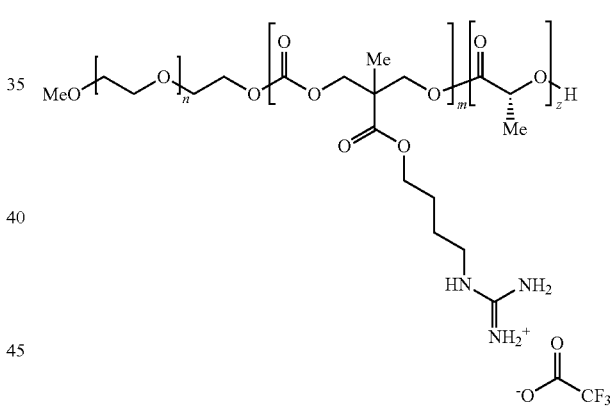

(M-6)

in which n is an integer selected such that the PEG subunit has an average molecular weight of about 5,000 Da, m is an integer ranging from 5 to 80, and z an integer ranging from 10 to 100.

No restriction is placed on the skeletal structure of the polymers described herein. In some embodiments of the invention, macromolecular chemotherapeutics include linear polymers, branched polymers, star polymers, mykto-arm star polymers, crosslinked polymers, ladder polymers, cyclic polymers, comb polymers, dendritic polymers, and graft polymers.

In some embodiments of the invention, a plurality of block copolymers form a micelle. The micelles can include block copolymers that include a water soluble block, a linker, and a cationic block. Embodiments of the invention include a micelle formed of a plurality of block copolymers. The micelles can include a plurality of macromolecular chemotherapeutics and can be homogeneous or heterogeneous. In some embodiments of the invention, micelles are mixed micelles including at least two different macromolecular chemotherapeutics. For example, in some embodiments of the invention, micelles include stereo complexes of macromolecular chemotherapeutics.

A person of ordinary skill in the art can select hydrophobic and hydrophilic portions of the macromolecular chemotherapeutic polymers to balance the hydrophobic and hydrophilic portions to drive self-assembly of the copolymers into micellar structures. In some embodiments, a stereo-complex includes, for example, paired complexes including triblock copolymers with poly L-lactide (PLLA) and poly D-lactide (PDLA).

Other exemplary macromolecular chemotherapeutic polymers according to embodiments of the invention include, but are not limited to, PEG(5k)-acetal-p[(MTC-Bn-cholesterol)8.05-ran-(MTC-Bn-dimethylhexylamine)3.44], PEG(5k)-acetal-p[(MTC-Bn-cholesterol)8.01-ran-(MTC-Bn-dimethylhexylamine)2.9], PEG(5k)-acetal-p[(MTC-Bn-cholesterol)3.99-ran-(MTC-Bn-dimethylhexylamine)3.49], PEG(5k)-acetal-p[(MTC-Bn-cholesterol)4.19-ran-(MTC-Bn-dimethylhexylamine)3.62], PEG(5k)-p[(MTC-OButylGuanidine)$_{10}$-PLLA$_{21}$, PEG(5k)-p[(MTC-OButylGuanidine)$_{20}$-PLLA$_{20}$, PEG(5k)-p[(MTC-OButylGuanidine)$_{60}$-PLLA$_{20}$, PEG(5k)-p[(MTC-OButylGuanidine)$_{10}$-PLLA$_{21}$, PEG(5k)-p[(MTC-OButylGuanidine)$_{10}$-PDLA$_{21}$, PEG(5k)-p[(MTC-OButylGuanidine)$_{20}$-PDLA$_{20}$, PEG(5k)-p[(MTC-OButylGuanidine)$_{60}$-PDLA$_{20}$, mPEG(5k)-p[(MTC-Bn-cholesterol)10], mPEG(5k)-acetal-p[(MTC-Bn-cholesterol)10], mPEG(5k)-p[(MTC-Bn-cholesterol)8-(MTC-Bn-Hexyl)3], mPEG(5k)-acetal-p[(MTC-Bn-cholesterol)8-(MTC-Bn-Hexyl)3.4], mPEG(5k)-p[(MTC-Bn-cholesterol)4.2-(MTC-Bn-Hexyl)3.5], and mPEG(5k)-p[(MTC-Bn-cholesterol)4.2-(MTC-Bn-Hexyl)3.6].

In some embodiments of the invention, a micelle includes a plurality of macromolecular chemotherapeutics. In some embodiments of the invention, the micelle has a diameter of 20 to 200 nm, such as from 50 to 200 nm, or from 50 to 100 nm. Macromolecular chemotherapeutics according to some embodiments of the invention can have a critical micelle concentration (CMC) of 1 to 50 micrograms per milliliters as measured in phosphate buffered saline.

In some embodiments of the invention, block copolymers are cleaved to form cytotoxic structures. In some embodiments of the invention, block copolymers are self-immolative. For example, in response to end-cap cleavage, macromolecular chemotherapeutics according to some embodiments of the invention can undergo head to tail depolymerization.

In some embodiments of the invention, pharmaceutical compositions include macromolecular chemotherapeutics. In some embodiments of the invention a pharmaceutical composition includes a plurality of macromolecular chemotherapeutics including a water soluble block, a cationic block, and a linker. In some embodiments of the invention, a pharmaceutical composition includes a plurality of micelles, wherein the micelles are formed of macromolecular chemotherapeutics.

The macromolecular chemotherapeutics can be used as stand-alone chemotherapeutic drugs and/or as a complex including the macromolecular chemotherapeutics and another biologically active material. In some embodiments of the invention, a pharmaceutical composition consists essentially of macromolecular chemotherapeutics, a solvent, and one or more excipients. Macromolecular chemotherapeutics can be present in a composition in an amount ranging from 0.1 μg to 200 μg/mL. The solvent can include a pharmaceutically acceptable aqueous solvent or mixtures of solvents, such as saline, water, ketones such as acetone, alcohols such as ethanol, and mixtures thereof.

A pharmaceutical composition can be administered topically, intravenously, subcutaneously, intramuscularly, transdermally, transmucosally, orally, by way of other body cavities, and/or by inhalation. Pharmaceutical compositions can have the form of a powder, a pill, a liquid, a paste, or a gel.

Some embodiments of the invention include methods of forming macromolecular chemotherapeutics. Macromolecular chemotherapeutics can be prepared by organocatalyzed ring-opening polymerization (ROP), for example to form an AB diblock polycarbonate. In some embodiments of the invention, resultant AB diblock copolymer can be quaternized with tertiary amines to provide the resultant cationic macromolecular therapeutics.

For example, in some embodiments of the invention, a macromolecular chemotherapeutic is prepared by organocatalyzed ROP of a cyclic carbonate monomer bearing a pendent protected derivative of an R2 group, as disclosed herein above, such as a pendent protected guanidine monomer (referred to herein for brevity as the "pendent monomer"). The ROP can produce an initial polymer containing a protected pendent monomer. Subsequent deprotection of the pendent monomer using a protic acid can form a cationic block including pendent R2 groups. Exemplary protic acids include hydrochloric acid, hydrobromic acid, sulfuric acid, phosphoric acid, trifluoroacetic acid, methanesulfonic acid, and p-toluenesulfonic acid.

The ROP reaction mixture can include the cyclic carbonate monomer, a nucleophilic initiator for the ROP, an organocatalyst, a solvent, and optionally an accelerator.

The ROP can be performed according to known methods. In some embodiments of the invention, the ROP can be performed at a temperature that is about ambient temperature or higher, such as 15° C. to 40° C. or 20° C. to 40° C. Reaction times can vary with solvent, temperature, agitation rate, pressure, and equipment, and can be complete within 1 to 100 hours.

The ROP reaction can be performed with a solvent. Solvents include for example, and not by way of limitation, dichloromethane, chloroform, and benzene. A suitable monomer concentration is, for example, 0.1 to 5 moles per liter. The ROP polymerizations can be conducted under an inert (i.e., dry) atmosphere, such as nitrogen or argon, and at a pressure of from 100 to 500 MPa (1 to 5 atm). At the completion of the reaction, the solvent can be removed using reduced pressure.

The polymeric components of exemplary stereocomplexes including macromolecular chemotherapeutics according to some embodiments of the invention can be formed, for example, as follows:
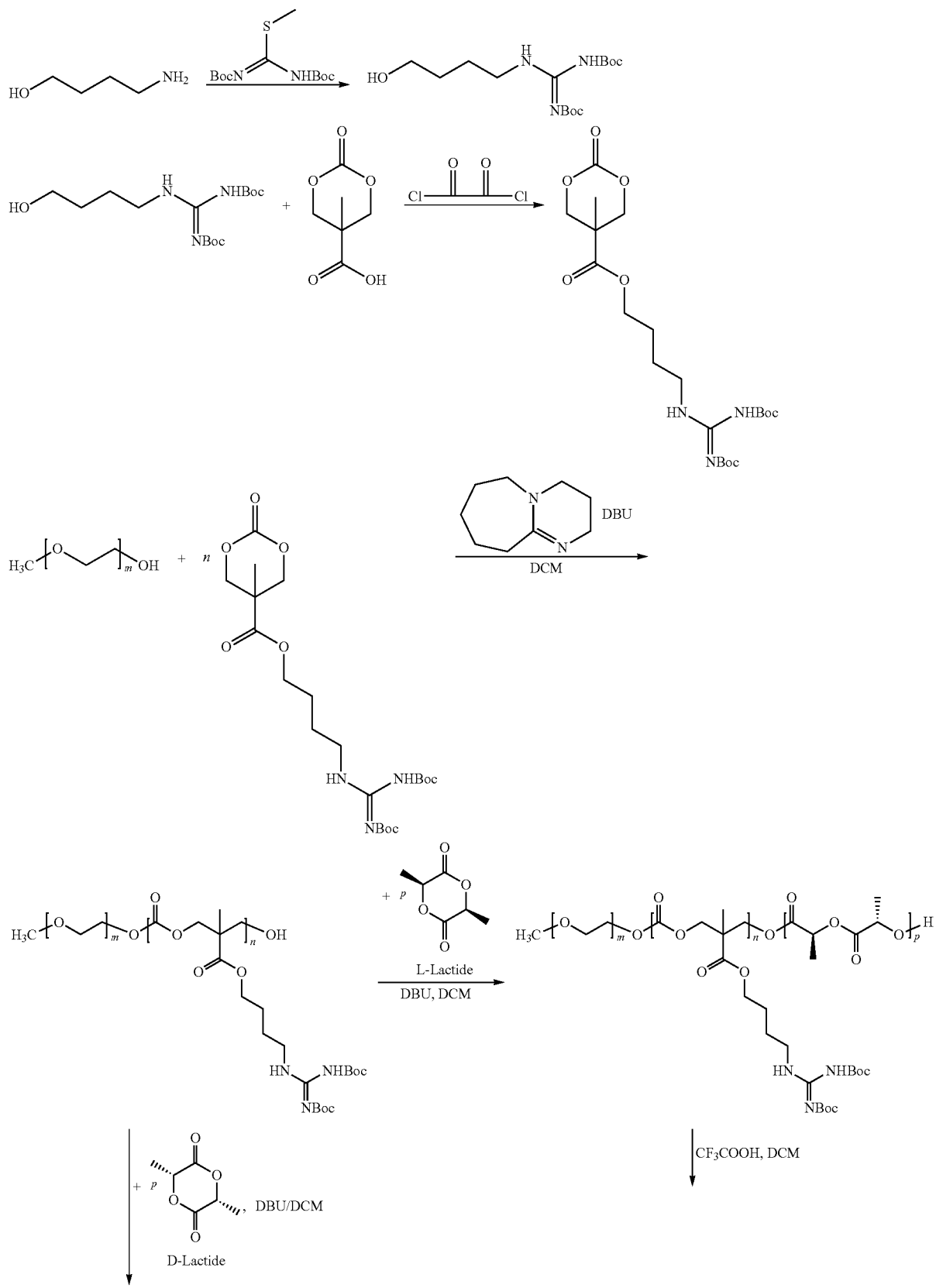

-continued

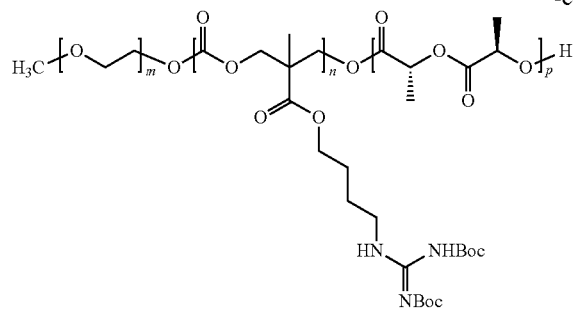

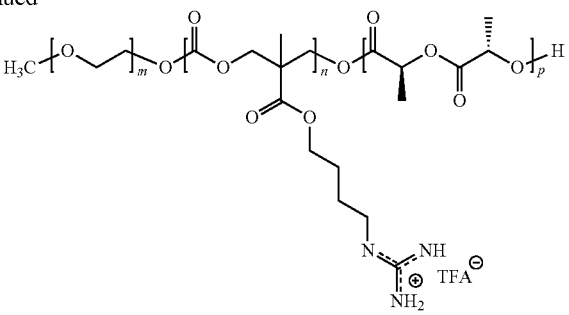

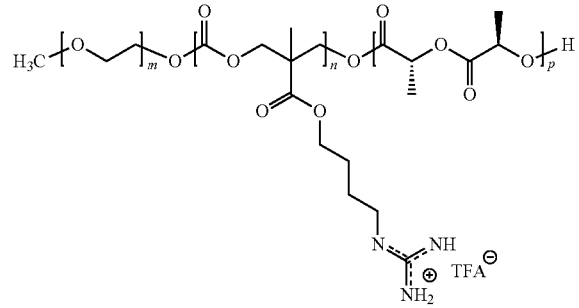

A person of ordinary skill in the art will be readily able to envisage adaptation of the above exemplary reaction scheme to prepare macromolecular chemotherapeutics of the desired structures.

Exemplary protecting groups include, but are not limited to benzyloxycarbonyl (Bnoc), tert-butyloxycarbonyl (tBoc, also referred to as "Boc"), and fluorenylooxycarbonyl (Fmoc) as shown below.

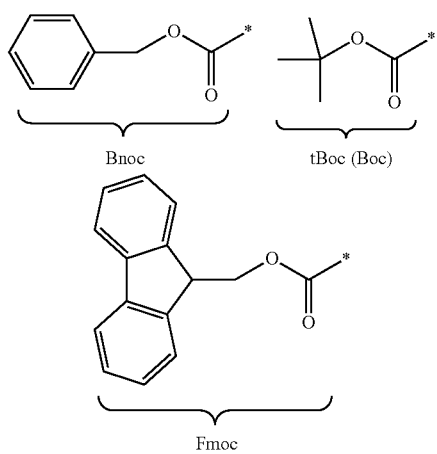

The Bnoc protecting group can be removed by acidolysis or catalytic hydrogenation. The Boc protecting group can be removed by acidolysis. The Fmoc protecting group can be removed by base, such as a secondary amineA Boc-protected guanidine nitrogen, for example, can be deprotected by treatment with a fluorinated carboxylic acid, such as trifluoroacetic acid.

The pendent monomers can independently be stereospecific or non-stereo specific. Exemplary non-limiting Boc-protected guanidine monomers, for instance, include the following structures, where n is an integer of 1 to 6:

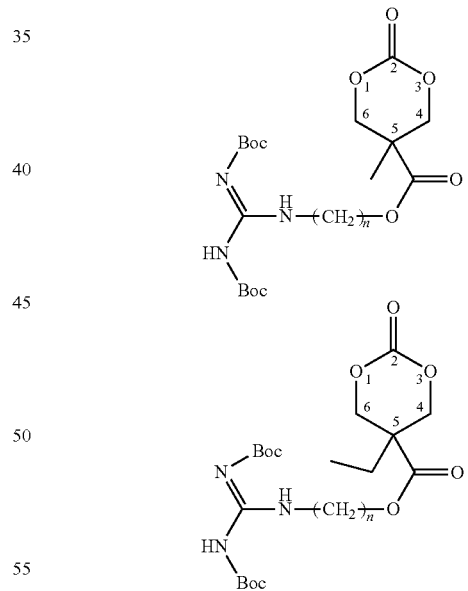

Another method of preparing the macromolecular chemotherapeutics includes polymerizing by organocatalyzed ROP a cyclic carbonate monomer bearing a pendent leaving group, which is capable of undergoing a nucleophilic substitution reaction. For instance, a nucleophilic substitution reaction with thiourea can form an isothiouronium group ionically associated with X', wherein X is an anionic form of the leaving group (X' is also a conjugate base of a protic acid). The cyclic carbonate monomer bearing the pendent leaving group is referred to herein as the "electrophilic monomer". Organocatalyzed ROP of the electrophilic monomer can produce an initial polymer having an electrophilic repeat unit. The electrophilic repeat unit can include a side chain bearing the leaving group.

Exemplary electrophilic monomers include, but are not limited to, the following cyclic carbonate monomers:

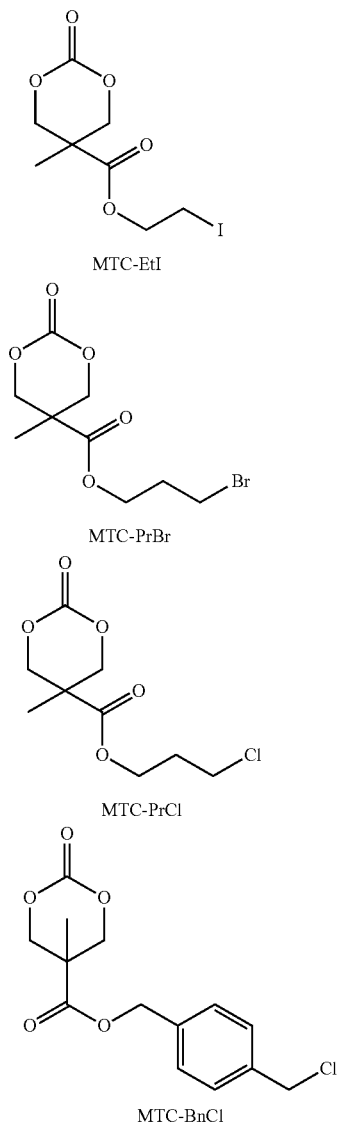

MTC-EtI

MTC-PrBr

MTC-PrCl

MTC-BnCl

In some embodiments of the invention, an ROP reaction mixture includes an initiator. The initiator can become a chain fragment that is covalently linked to a repeat unit of the ring opened polymer chain. Initiators for ring opening polymerizations generally include nucleophilic groups such as alcohols, primary amines, secondary amines, thiols, and combinations thereof. The initiator can include one or more active nucleophilic initiator groups. For example, the initiator can be a polyether having a terminal alcohol, polyether having a terminal amine group, or a polymer having a terminal thiol group. In some embodiments of the invention, the ROP initiator is an alcohol. The ROP initiator can be any suitable alcohol. Exemplary initiators include, but are not limited to, methanol, ethanol, propanol, stearyl alcohol, nonadecyl alcohol, saccharides, ethylene glycols, propylene glycols, and BnMPA, derived from 2,2-dimethylol propionic acid, and mono-nucleophilic polymeric ROP initiators including endcapped poly(ethylene glycols), such as monomethyl poly(ethylene glycol) (mPEG-OH)), and di-nucleophilic polyether ROP initiators, such as include poly(ethylene glycol). The number average molecular weight (Mn) of the di-nucleophilic polyether initiator can be from 100 to 50000, such as 1000 to 5000 daltons.

Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines. Exemplary organocatalysts include, but are not limited to, N-bis(3,5-trifluoromethyl)phenyl-N'-cyclohexyl-thiourea (TU), 1,1,1,3,3,3-hexafluoropropan-2-ol-2-yl (HFP) group.

The ROP catalyst can be added in a proportion of 1/20 to 1/40,000 moles relative to the cyclic monomers, such as in a proportion of 1/1,000 to 1/20,000 moles relative to the cyclic monomers.

The ROP polymerization can be conducted in the presence of an optional accelerator, such as a nitrogen base. Exemplary nitrogen base accelerators include, for example, pyridine (Py), N,N-dimethylaminocyclohexane (Me2NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), and 7-methyl-1,5,7-triazabicyclo[4.4.0]dec-5-ene (MTBD).

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst can be present in an amount of 0.2 to 20 mol %, 0.5 to 10 mol %, 1 to 5 mol %, or 1 to 2.5 mol %, based on total moles of cyclic monomer. The accelerator, when used, can be present in an amount of 0.1 to 5.0 mol %, 0.1 to 2.5 mol %, 0.1 to 1.0 mol %, or 0.2 to 0.5 mol %, based on total moles of cyclic monomer.

The amount of initiator can be calculated based on the equivalent molecular weight per participating nucleophilic initiator group in the ring opening polymerization. The participating initiator groups can be present in an amount of 0.001 to 10.0 mol % based on the total moles of cyclic monomers used in the polymerization. For example, if the molecular weight of the initiator is 100 g/mole and the initiator has two participating hydroxyl initiator groups, the equivalent molecular weight per hydroxyl group is 50 g/mole. If the polymerization calls for 5 mol % reactive hydroxyl groups per mole of cyclic carbonyl monomers, the amount of initiator is 0.05×50=2.5 g per mole of cyclic carbonyl monomers.

The catalysts can be removed by selective precipitation or in the case of the solid supported catalysts, by filtration. The initial polymer formed by the ROP can comprise residual catalyst in an amount greater than 0% by weight, based on total weight of the initial polymer and the residual catalyst.

Optionally, the initial cationic subunit polymer (i.e., prior to deprotection) formed by the ROP can be endcapped. An endcap agent can prevent further chain growth and stabilize the reactive end groups, minimizing unwanted side reactions such as chain scission during and/or after the deprotection step or treatment with thiourea. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap group can be a biologically active moiety.

In some embodiments of the invention, macromolecular chemotherapeutics degrade to form cytotoxic molecules. In some embodiments of the invention, compositions including macromolecular chemotherapeutics have a half inhibitory concentration (IC50) in cancer cells of 10 to 250 milligrams per liter (mg/L), such as 50 to 100 mg/L. In some embodiments of the invention, macromolecular chemotherapeutics inhibit the growth of cancer stem cells.

In some embodiments of the invention, micelles are stable in PBS-serum solution. As used herein, "stable in PBS-serum solution" means that the particle size of the micelles did not change significantly in PBS solution containing 10% serum over a 24 hour time period.

Embodiments of the invention include a method of treating cancer, for example in a mammal or a human in need thereof. The methods can include, for example, administering to a mammal in need thereof, an effective amount of a pharmaceutical composition. The pharmaceutical composition can include a block copolymer including a water-soluble block, a cationic block, and a cleavable linker, wherein the cleavable linker is connected to the water-soluble bock and the charged block.

Figure 7:
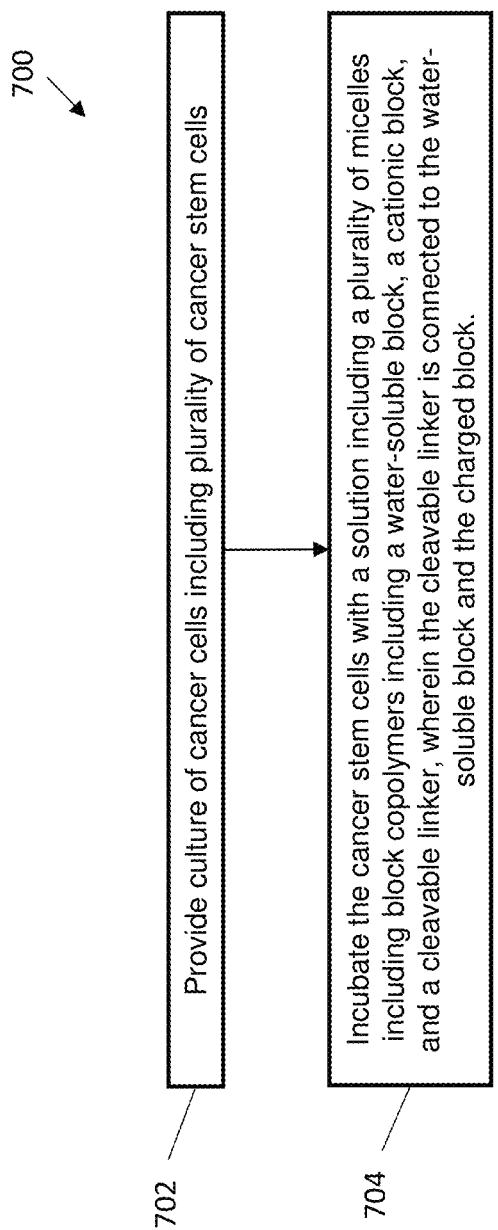
FIG. 7 depicts a flow diagram of a method for inhibiting cancer stem cell growth according to exemplary embodiments of the invention.

FIG. 7 depicts a flow diagram of a method 700 for inhibiting cancer stem cell growth. The method 700 includes, as shown at block 702, providing a culture of cancer cells including a plurality of cancer stem cells. The method also includes incubating the cancer stem cells with a solution including a plurality of micelles, including block copolymers including a water soluble block, a cationic block, and a cleavable linker, wherein the cleavable linker is connected to the water-soluble block and the charged block, as shown at block 704.

Figure 8:
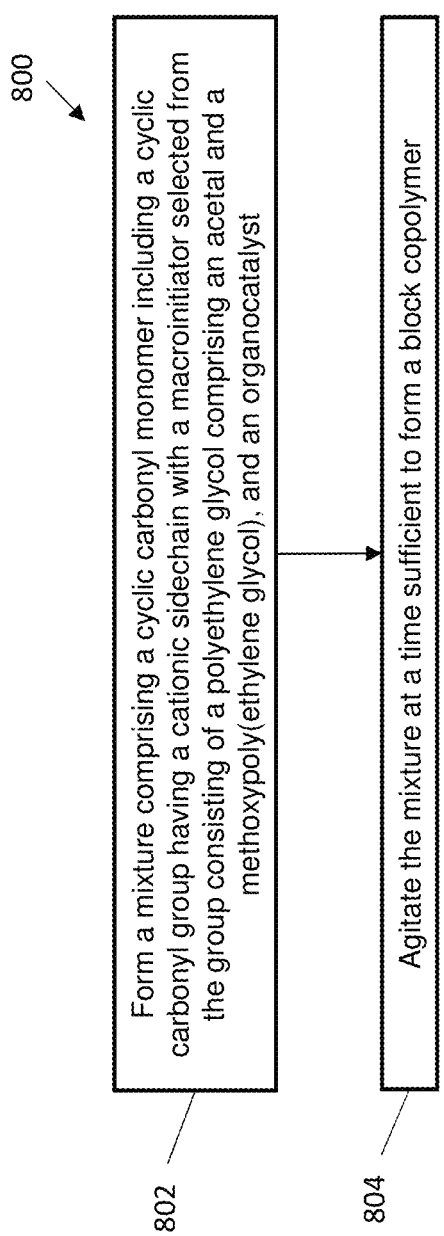
FIG. 8 depicts a flow diagram of a method for synthesizing a macromolecular chemotherapeutic according to exemplary embodiments of the invention.

FIG. 8 depicts a flow diagram of an exemplary method 800 for synthesizing a macromolecular chemotherapeutic. The method 800 includes, as shown at block 802, forming a mixture including a cyclic carbonyl monomer comprising a cyclic carbonyl group having a cationic sidechain with a macroinitiator selected from the group consisting of a polyethylene glycol comprising an acetal and a methoxypoly (ethylene glycol), and an organocatalyst. The method also includes agitating the mixture at a time sufficient to form a block copolymer, as shown at block 804.

Example 1

A plurality of macromolecular chemotherapeutic molecules was prepared by organo-catalyzed ring opening polymerization of a cyclic benzyl chloride functionalized polycarbonate monomer and either mPEG (5000 Da) or acetal containing PEG (about 5000 Da) as the macroiniators. The resultant polymers were quaternized with an amine functionalized cholesterol derivative (1a) and (1b), or with a combination of an amine functionalized cholesterol derivative and N,N-dimethylhexylamine (1c-1f). The polymers thus formed were as follows:

| | |
|---|---|
| 1a | mPEG(5k)-p[(MTC-Bn-cholesterol)10] |
| 1b | mPEG(5k)-acetal-p[(MTC-Bn-cholesterol)10] |
| 1c | mPEG(5k)-p[(MTC-Bn-cholesterol)8-(MTC-Bn-Hexyl)3] |
| 1d | mPEG(5k)-acetal-p[(MTC-Bn-cholesterol)8-(MTC-Bn-Hexyl)3.4] |
| 1e | mPEG(5k)-p[(MTC-Bn-cholesterol)4.2-(MTC-Bn-Hexyl)3.5] |
| 1f | mPEG(5k)-p[(MTC-Bn-cholesterol)4.2-(MTC-Bn-Hexyl)3.6] |

The micellar nanoparticles were prepared by self-assembly of the polymers in sterile PBS at 1 mg/mL. The solution was briefly vortexed for 1 min then sonicated in a water bath for around 1 h to make sure that the polymers were fully dissolved. The particle size, polydispersity and zeta potential of the nanoparticles were characterized by dynamic light scattering. The critical micelle concentration (CMC) of the polymers in water was determined by fluorescence spectroscopy using pyrene as a probe.

The cytotoxicity of the polymeric micelles or doxorubicin (DOX) was studied by MTT assay. Hep3B, MCF7 or MCF7/Adr cells were seeded onto 96-well plates. After 24 h, the culture media was replaced with fresh media containing various concentrations of the polymers ranging from 0.98 to 1000 µg/mL or media containing various concentrations of DOX ranging from 0.01 to 10 µg/mL. After 72 h incubation (or 24 h incubation for Hep3B treated with DOX), the media was replaced by 100 µL of fresh media containing 20 µL MTT solution. A shorter incubation time was used for DOX as most cells died even at very low DOX concentrations. The cells were then returned to the incubator for 4 h. The MTT-containing media was replaced with 150 µL DMSO. The absorbance of the solution in each well was determined using a microplate spectrophotometer at 550 nm and 690 nm (reference). The IC50 values of the polymers were determined as the polymer concentration where 50% viability of cells was achieved.

Characteristics of polymers 1a-1f are summarized in the following Table 1.

TABLE 1

| Sample | CMC (ppm) | Size (nm) | PDI | Zeta potential (mV) | IC50 (mg/L) Hep38 | IC50 (mg/L) HepG2 | IC50 (mg/L) SNU423 |
|---|---|---|---|---|---|---|---|
| 1a | 7.5 | 55.8 +/− 0.6 | 0.37 +/− 0.02 | 0.9 +/− 0.4 | 72 | 80 | 160 |
| 1b | 7.8 | 88.9 +/− 2.6 | 0.30 +/− 0.02 | 1.4 +/− 0.5 | 85 | 80 | 170 |
| 1c | 11.4 | 23.2 +/− 0.2 | 0.13 +/− 0.02 | 1.5 +/− 1.1 | 46 | 40 | 45 |
| 1d | 12.2 | 74.4 +/− 0.3 | 0.22 +/− 0.01 | 4.6 +/− 1.3 | 40 | 45 | 45 |
| 1e | 13.5 | 53.3 +/− 0.3 | 0.18 +/− 0.01 | 1.4 +/− 0.2 | 52 | 62 | 90 |
| 1f | 17.3 | 106.2 +/− 0.8 | 0.21 +/− 0.01 | 0.9 +/− 0.3 | 45 | 62 | 90 |

Figure 1A:
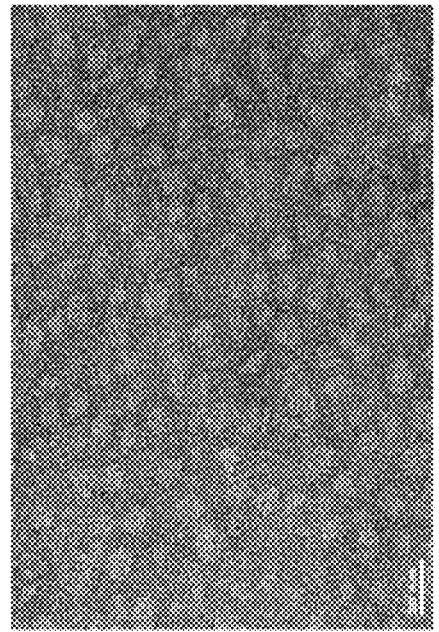
FIG. 1A depicts TEM image of macromolecular chemotherapeutics according to exemplary embodiments of the invention.

The morphology of self-assembled micellar nanoparticles was observed under TEM. FIG. 1A depicts a TEM image of polymer 1e. FIG. 1B depicts a TEM image of polymer 1c.

Example 2

Hep3B cells were seeded onto 6-well plates at a density of 1.6×10$^5$ cells per 2 mL DMEM per well. After 24 h, the plating media was replaced with fresh DMEM containing various concentrations of polymers: IC50 and 2×IC50. Cells were harvested after 4, 24, 48 or 72 h incubation, and stained using the Alexa Fluor® 488 annexin V/Dead Cell Apoptosis Kit with Alexa® Fluor 488 annexin V and PI for flow cytometry (Invitrogen, Singapore) according to the manufacturer's instructions. The labeled cells were subjected to flow cytometry analysis (BD FACSAria II, Singapore).

Figures 2A, 2B, 2C:
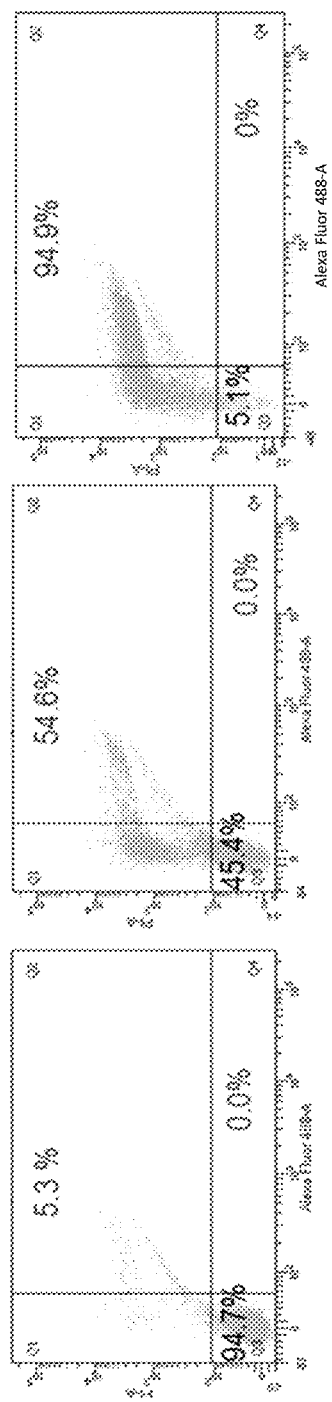
FIGS. 2A-2C depict the percentage of live, apoptotic, and necrotic Hep3B cells after exposure to macromolecular chemotherapeutics according to exemplary embodiments of the invention.
Figures 3A, 3B, 3C:
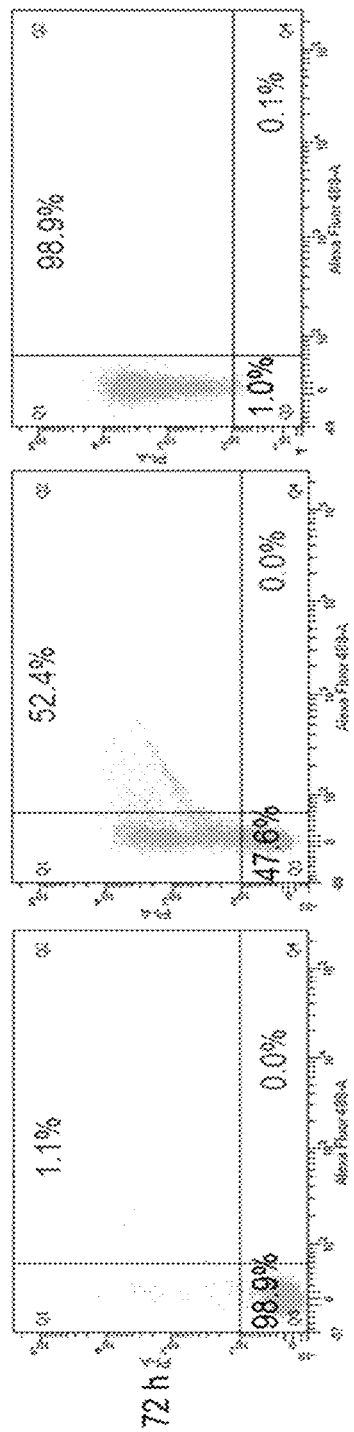
FIGS. 3A-3C depict the percentage of live, apoptotic, and necrotic Hep3B cells after exposure to macromolecular chemotherapeutics according to exemplary embodiments of the invention.

FIGS. 2A-2C depict the percentage of live, apoptotic, and necrotic Hep3B cells after exposure to polymer 1c for 4 hours, in which FIG. 2A is a control, FIG. 2B reflects IC50, and FIG. 2C reflects 2×IC50. FIGS. 3A-3C depict the percentage of live, apoptotic, and necrotic Hep3B cells after exposure to polymer 1c for 72 hours, in which FIG. 3A is a control, FIG. 3B reflects IC50, and FIG. 3C reflects 2×IC50.

Example 3

Activity against drug-resistant cancer cells (MCF-7/ADR or BCap-37/MDR transfected with a multidrug resistant gene), cancer stem cells and prevention of drug resistance development was investigated through cytotoxicity studies. The cytotoxicity of the polymeric micelles or DOX was studied by MTT assay according to known methods. The absorbance of the solution in each well was determined using a microplate spectrophotometer at 550 nm and 690 nm. The IC50 values of the polymers were determined as the polymer concentration where 50% viability of cells was achieved.

Figure 4A:
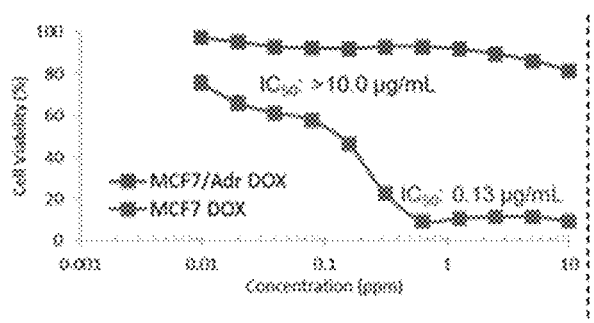
FIGS. 4A and 4B depict charts of cell viability versus concentration for macromolecular chemotherapeutics according to exemplary embodiments of the invention.
Figure 4B:
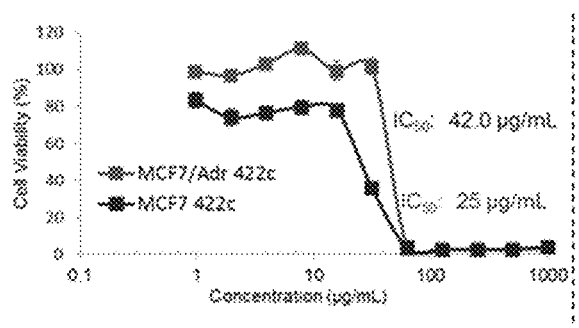

FIGS. 4A and 4B depict charts of cell viability versus concentration for MCF-7/ADr cells and MCF-7 cells for DOX treated cells (FIG. 4A) and cells exposed to polymer 1c (FIG. 4B).

Figure 5A:
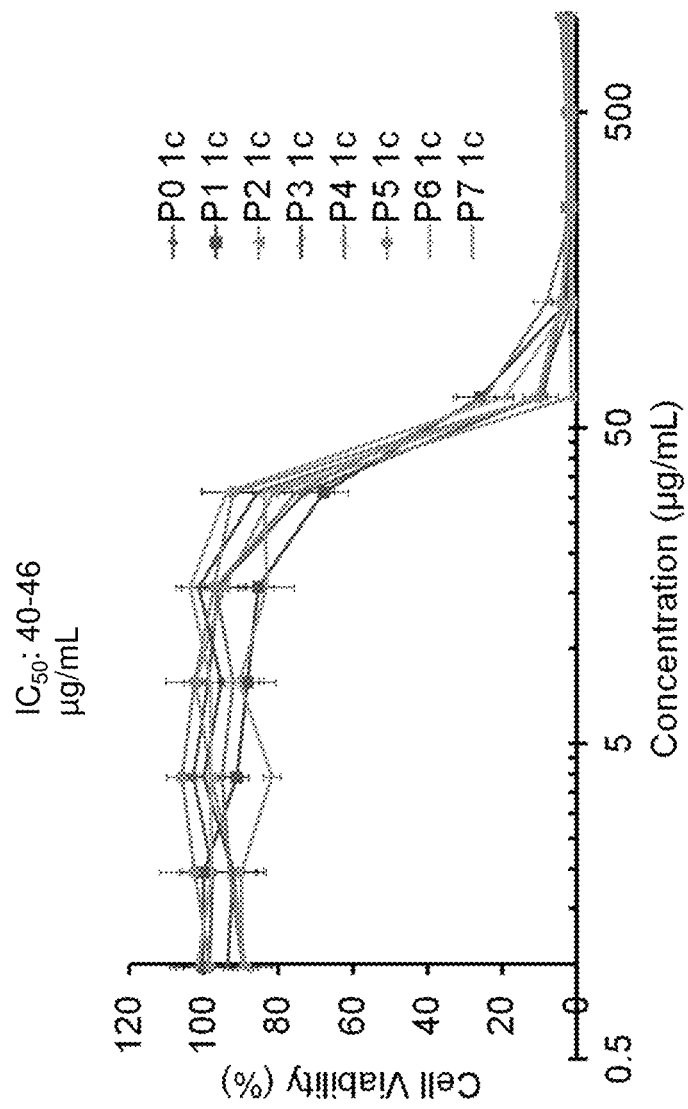
FIGS. 5A and 5B depict charts of cell viability versus concentration for macromolecular chemotherapeutics according to exemplary embodiments of the invention.
Figure 5B:
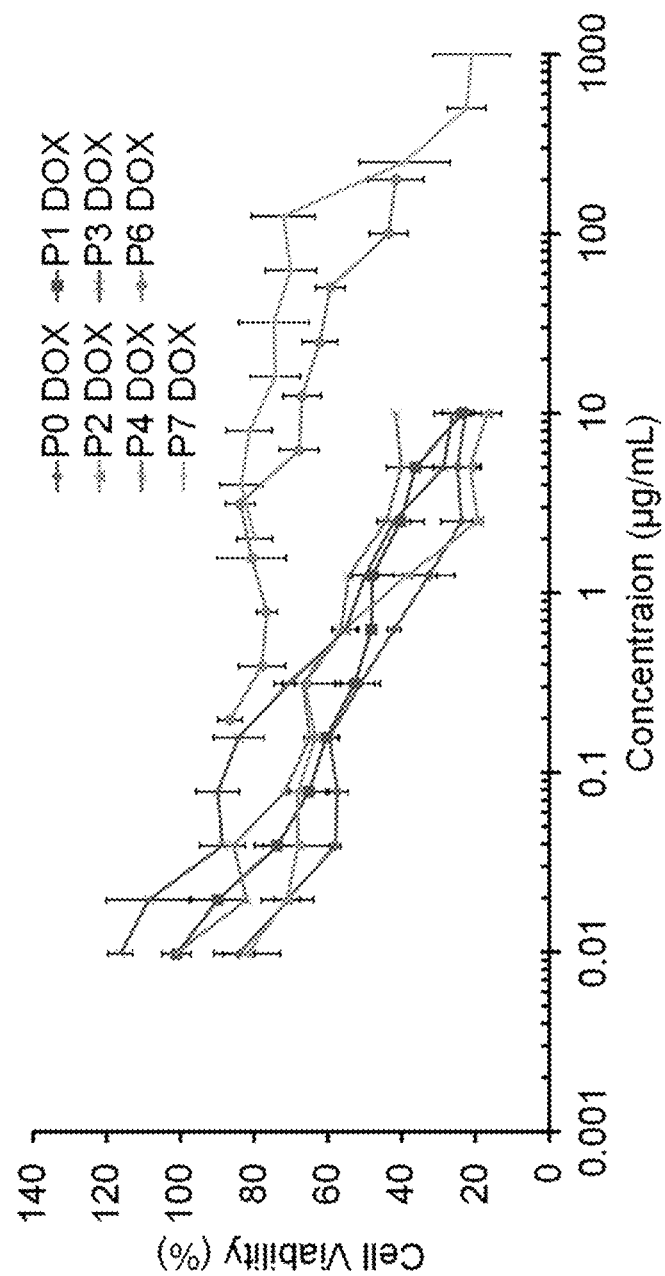

FIGS. 5A and 5B depict charts of cell viability versus concentration for Hep3B cells after each pulse treatment with polymer 1c (FIG. 5A) and DOX (FIG. 5B). To perform the pulse treatment to evaluate whether multiple treatments would induce resistance, cells were exposed to polymer or DOX for times of 1, 2, 4, 12, 24, and 72 hours. After each treatment, IC50 values of polymer and DOX were measured.

Figures 6A, 6B:
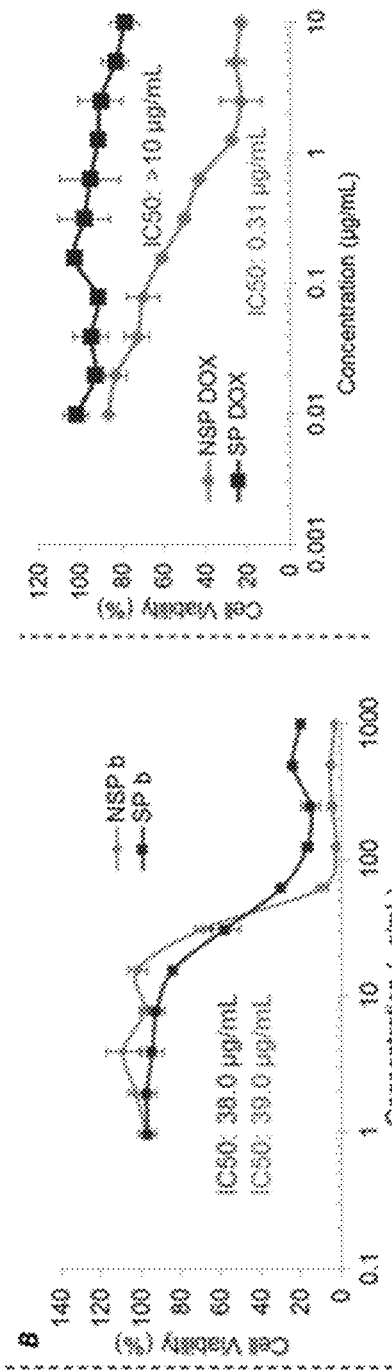
FIGS. 6A and 6B depict charts of cell viability versus concentration for macromolecular chemotherapeutics according to exemplary embodiments of the invention.

FIGS. 6A and 6B depict charts of cell viability versus concentration for cancer stem cells (SP) and non-cancer stem cells (NSP) for doxorubicin treated cells (FIG. 6A) and cells exposed to polymer 1c (FIG. 6B). To obtain the stem cells, Hep3B cancer stem cells were sorted by SP assay according to known methods. Dead cells were excluded, and the live cells were analyzed and sorted by a dual wavelength analysis. The identity of cancer stem cells was evaluated by immunostaining.

To evaluate the effect of polymer or DOX on the SP and NSP cells, freshly sorted Hep3B SP and NSP cells were re-suspended in media and seeded onto 96 well plates, and incubated for 48 h. The medium was replaced by fresh medium containing various concentrations of the polymers (0.98-1000 μg/mL) or DOX (0.01-10 μg/mL). Cells treated with the polymers were incubated for 72 h, and cells treated with DOX were incubated for 24 h. At the end of the incubation, the viability of cells was evaluated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A macromolecular chemotherapeutic, comprising:
   a block copolymer comprising:
      a water-soluble block,
      a cationic block, the cationic block comprising a polymeric subunit comprising a polycarbonate backbone having from 4 to 8 atoms;
      a linker, wherein the linker is connected to the water-soluble bock and the charged block; and
      an endcap bound to the cationic block having the structure:

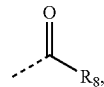

wherein which R8 is a long chain alkyl group, a polylactide, or a cholesterol.

2. The macromolecular chemotherapeutic of claim 1, wherein the water-soluble block comprises polyethylene oxide.

3. The macromolecular chemotherapeutic of claim 2, wherein the polyethylene oxide has an average molecular weight of 2000 to 20,000 daltons.

4. The macromolecular chemotherapeutic of claim 1, wherein the linker is a cleavable linker.

5. The macromolecular chemotherapeutic of claim 3, wherein the cleavable linker comprises an acetal or a disulfide.

6. The macromolecular chemotherapeutic of claim 1, wherein the cationic block includes polymeric subunit comprising a polycarbonate backbone having from 6 to 8 atoms.

7. A method of inhibiting cancer stem cell growth comprising:
   providing a culture of cancer cells, comprising a plurality of cancer stem cells;
   incubating the cancer stem cells with a solution comprising a plurality of micelles, wherein the micelles comprise the macromolecular chemotherapeutic of claim.

8. The method of claim 7, wherein the cationic block includes a polymeric subunit comprising a polycarbonate backbone having from 6 to 8 atoms.

9. A method of treating cancer, comprising:
   administering to a mammal in need thereof an effective amount of a pharmaceutical composition, wherein the pharmaceutical composition comprises the chemotherapeutic of claim 1.

10. The method of claim 9 further comprising killing cancer cells of the mammal by necrosis.

11. The method of claim 9, wherein the water-soluble block comprises polyethylene oxide.

12. The method of claim 11, wherein the polyethylene oxide has an average molecular weight of 2000 to 20,000 daltons.

13. The method of claim 9, wherein the cleavable linker comprises an acetal.

14. The method of claim 9, wherein the cleavable linker comprises a disulfide.

15. A method of synthesizing the macromolecular chemotherapeutic of claim 1, comprising:
   forming a mixture comprising a cyclic carbonyl monomer comprising a cyclic carbonyl group having a cationic sidechain with a macroinitiator selected from the group consisting of a polyethylene glycol comprising an acetal and a methoxypoly(ethylene glycol), and an organocatalyst, and agitating the mixture at a time sufficient to form a block copolymer.

16. The method of claim 15, wherein the mixture comprises an accelerator.

17. The method of claim 15 further comprising combining the block copolymer with a tertiary amine.

18. The method of claim 17, wherein the tertiary amine comprises cholesterol or a cholesterol derivative.

19. The method of claim 15, wherein the block copolymer is self-immolative at a pH less than or equal to 6.5.

* * * * *